US010427142B1

(12) United States Patent
Al-Herz et al.

(10) Patent No.: US 10,427,142 B1
(45) Date of Patent: Oct. 1, 2019

(54) METHODS FOR SYNTHESIZING HIERARCHICAL ZEOLITES FOR CATALYTIC CRACKING

(71) Applicants: Saudi Arabian Oil Company, Dhahran (SA); King Fahd University of Petroleum and Minerals, Dhahran (SA)

(72) Inventors: Mansour Ali Al-Herz, Al-Ahsa (SA); Musaed Salem Al-Ghrami, Dhahran (SA); Mohammed Abdul Bari Siddiqui, Dhahran (SA); Mian Rahat Saeed, Dhahran (SA); Rabindran Jermy Balasamy, Dhahran (SA)

(73) Assignees: KING FAHD UNIVERSITY OF PETROLEUM AND MINERALS, Saudi Arabia (SA); SAUDI ARABIAN OIL COMPANY (SA)

(*) Notice: Subject to any disclaimer, the term of this patent is extended or adjusted under 35 U.S.C. 154(b) by 0 days.

(21) Appl. No.: 16/369,589

(22) Filed: Mar. 29, 2019

Related U.S. Application Data

(62) Division of application No. 16/103,623, filed on Aug. 14, 2018.

(51) Int. Cl.
| | |
|---|---|
| *C10G 11/05* | (2006.01) |
| *B01J 29/40* | (2006.01) |
| *B01J 35/10* | (2006.01) |
| *B01J 37/30* | (2006.01) |
| *B01J 37/28* | (2006.01) |
| *B01J 29/78* | (2006.01) |
| *B01J 29/70* | (2006.01) |
| *B01J 29/89* | (2006.01) |
| *C01B 39/06* | (2006.01) |
| *C01B 39/02* | (2006.01) |
| *C01B 39/36* | (2006.01) |
| *C01B 39/42* | (2006.01) |
| *C01B 39/44* | (2006.01) |
| *B01J 29/65* | (2006.01) |
| *B01J 29/04* | (2006.01) |
| *B01J 37/02* | (2006.01) |
| *C10G 11/04* | (2006.01) |

(Continued)

(52) U.S. Cl.
CPC ........... *B01J 29/405* (2013.01); *B01J 29/041* (2013.01); *B01J 29/045* (2013.01); *B01J 29/40* (2013.01); *B01J 29/65* (2013.01); *B01J 29/655* (2013.01); *B01J 29/7034* (2013.01); *B01J 29/7049* (2013.01); *B01J 29/7869* (2013.01); *B01J 29/89* (2013.01); *B01J 35/109* (2013.01); *B01J 37/0201* (2013.01); *B01J 37/28* (2013.01); *B01J 37/30* (2013.01); *C01B 39/026* (2013.01); *C01B 39/06* (2013.01); *C01B 39/065* (2013.01); *C01B 39/36* (2013.01); *C01B 39/365* (2013.01); *C01B 39/42* (2013.01); *C01B 39/44* (2013.01); *C07C 4/06* (2013.01); *C10G 11/04* (2013.01); *C10G 11/05* (2013.01); *C10G 11/18* (2013.01); *B01J 2219/00844* (2013.01); *B01J 2229/10* (2013.01); *B01J 2229/126* (2013.01); *B01J 2229/18* (2013.01); *B01J 2229/183* (2013.01); *B01J 2229/186* (2013.01); *B01J 2229/34* (2013.01); *B01J 2229/37* (2013.01); *B01J 2229/38* (2013.01); *B01J 2229/42* (2013.01); *B01J 2523/3706* (2013.01); *B01J 2523/51* (2013.01); *B01J 2523/72* (2013.01); *C10G 2300/1037* (2013.01); *C10G 2300/1066* (2013.01); *C10G 2300/1081* (2013.01); *C10G 2300/40* (2013.01); *C10G 2400/02* (2013.01); *C10G 2400/20* (2013.01)

(58) Field of Classification Search
CPC ......... C10G 11/04; C10G 11/05; C10G 11/18; C10G 2300/40; C10G 2300/1037; C10G 2300/1066; C10G 2300/1081; C10G 2400/02; C10G 2400/20; C07C 4/06
USPC ................. 585/648, 653; 208/113, 118, 119, 208/120.01, 121, 122
See application file for complete search history.

(56) References Cited

U.S. PATENT DOCUMENTS

| | | |
|---|---|---|
| 4,358,397 A | 11/1982 | Chu |
| 5,976,356 A | 11/1999 | Drake et al. |
| 6,300,537 B1 | 10/2001 | Strohmaier et al. |

(Continued)

FOREIGN PATENT DOCUMENTS

| | | |
|---|---|---|
| CN | 102530980 A | 7/2012 |
| CN | 104148107 B | 3/2016 |
| WO | 2013123299 A1 | 8/2013 |

OTHER PUBLICATIONS

Dongare, et al., "Synthesis, characterization, and catalytic properties of [Zr]-ZSM-5"; Catalysis Today; 1999; vol. 49, Issues 1-3, pp. 267-276.

(Continued)

*Primary Examiner* — Elizabeth D Wood
(74) *Attorney, Agent, or Firm* — Bracewell LLP; Constance Gall Rhebergen

(57) ABSTRACT

Provided here are zirconium-substituted hierarchical zeolite compositions and methods of preparing such catalytic compositions. One such method involves subjecting the zirconium-substituted zeolite to a framework modification process using a single template to produce a framework-modified zeolite, followed by subjecting the framework-modified zeolite to an ion exchange process to produce a hierarchical zeolite composition. Also provided are methods of catalytic cracking of hydrocarbon feedstocks using these zirconium-substituted hierarchical zeolite compositions.

20 Claims, 14 Drawing Sheets

(51) Int. Cl.
*C10G 11/18* (2006.01)
*C07C 4/06* (2006.01)

(56) References Cited

U.S. PATENT DOCUMENTS

| | | |
|---|---|---|
| 6,521,563 B2 | 2/2003 | Strohmaier et al. |
| 6,548,725 B2 | 4/2003 | Froment et al. |
| 6,566,293 B1 | 5/2003 | Vogt et al. |
| 6,669,924 B1 | 12/2003 | Kaliaguine et al. |
| 7,686,942 B2 | 3/2010 | Xie et al. |
| 7,807,132 B2 | 10/2010 | Garcia-Martinez |
| 8,614,160 B2 | 12/2013 | Upson et al. |
| 8,653,315 B2 | 2/2014 | Ali |
| 8,658,127 B2 | 2/2014 | Holland |
| 8,821,714 B2 | 9/2014 | Chaumonnot et al. |
| 8,951,498 B2 | 2/2015 | Larsen et al. |
| 9,168,515 B2 | 10/2015 | Wang et al. |
| 2006/0052236 A1 | 3/2006 | Angevine et al. |
| 2013/0184147 A1 | 7/2013 | Ryoo et al. |
| 2015/0094511 A1 | 4/2015 | Bastianti et al. |
| 2016/0017238 A1 | 1/2016 | Stamires et al. |
| 2016/0129429 A1* | 5/2016 | Kegnæs ............... C01B 37/005 585/467 |
| 2016/0137516 A1* | 5/2016 | Kegnæs ............... B01J 29/89 585/467 |

OTHER PUBLICATIONS

Konno, et al., "Effectiveness of nano-scale ZSM-5 zeolite and its deactivation mechanism on catalytic cracking of representative hydrocarbons of naphtha"; Micorporous and Mesoporous Materials; 2013; vol. 175, pp. 25-33.

Koohsaryan, et al., "Nanosized and Hierarchical Zeolites: A Short Review". Chinese Journal of Catalysis; 2016; vol. 37, No. 4, pp. 447-467.

Lee, et al., "Controlled decationization of X zeolite: mesopore generation within zeolite crystallites for bulky molecular adsorption and transformation", Journal of Materials Chemistry A; 2013; vol. 1, pp. 12096-12102.

Shah, et al., "Synthesis and characterization of isomorphously zirconium substituted Mobil Five (MFI) zeolite"; Materials Chemistry and Physics; 2012; vol. 134, pp. 43-49.

Song, et al.,"Production of Propylene from Ethanol Over ZSM5 Zeolites". Catalyst Letters; 2009, vol. 131, pp. 364-369.

Verboekend, et al., Synthesis, characterisation, and catalytic evaluation of hierarchical faujasite zeolites: milestones, challenges, and future directions; 2016; Chem. Soc. Rev., 2016, vol. 45, pp. 3331-3352.

Wang, et al., "Synthesis and catalytic Reaction of [Zr] ZSM-5"; Studies in Surface Science and Catalysis; 1994; vol. 83, pp. 67-74.

Zhang, et al., "Innovations in Hierarchical Zeolites Synthesis"., Catalysis Today; 2016; vol. 264, pp. 3-15.

Zhang et al. "Nano-crystallite oriented self-assembled ZSM-5 zeolite and its LPDE cracking properties: Effects of accessibility and strength of acid sites." Journal of Catalysis; 2013; vol. 302, pp. 115-125.

* cited by examiner

METHODS FOR SYNTHESIZING HIERARCHICAL ZEOLITES FOR CATALYTIC CRACKING

CROSS-REFERENCE TO RELATED APPLICATION

This application is a divisional application of and claims priority to and the benefit of U.S. patent application Ser. No. 16/103,623, filed Aug. 14, 2018, the entire disclosure of which is incorporated here by reference.

FIELD

This disclosure relates to methods of making and using hierarchical zeolites, specifically as catalysts for cracking of petroleum feedstocks.

BACKGROUND

The high severity-fluid catalytic cracking (HS-FCC) process has shown the potential for converting refinery streams containing heavy oils into product streams containing light olefins. These light olefins are suitable for producing large amounts of propylene and high-octane gasoline. The HS-FCC process is capable of producing yields of propylene up to four times greater than the traditional FCC units with greater conversion levels for a range of petroleum steams. Achieving maximum propylene yield and effective conversion from various feedstock with a wide range of qualities presents considerable challenges to the catalyst design for the HS-FCC. The conventional feedstocks for the FCC range from hydrocracked bottoms to heavy feed fractions such as vacuum gas oil and atmospheric residue. However, these feedstocks are limited and obtained through costly and energy intensive refining steps, and thus, not expected to fulfill the growing market demands.

A typical FCC catalyst consists of zeolite, active matrix (additive), inactive matrix (filler), and the binder. The first two components are the main drivers for cracking the feed in the process. The filler and the binder contribute to the overall activity of the catalyst by providing proper particle strength and morphology. Presence of zeolites in a HS-FCC catalyst improves the yield of light olefins due to its shape selectivity, special pore structure, and greater specific surface area. However, when the crystal size of the zeolites is close to the molecular diameter of light hydrocarbons, the diffusion of the reactant or product molecules within the micropores is usually the rate-limiting step of the reaction. Furthermore, coke formation on the crystal surface is favored under diffusion-controlled regime, which obstructs the accessibility of the pores, and thus deactivates the catalyst.

SUMMARY

Various embodiments in this disclosure were developed to address these shortcomings in the art. To control coke formation and to reduce diffusion limitations of reactant and product hydrocarbons, micro/mesoporous-crystalline zeolites were produced with low diffusion resistance and greater external surface area.

Embodiments include methods of making hierarchical zeolite compositions. One such method includes the steps of subjecting an initial zeolite and a zirconium source to a partial isomorphous substitution process to produce a zirconium-substituted zeolite; then, subjecting the zirconium-substituted zeolite to a framework modification process using a single template to produce a framework-modified zeolite; and subjecting the framework-modified zeolite to an ion exchange process to produce a hierarchical pore structure in at least a portion of the framework-modified zeolite, resulting in the hierarchical zeolite composition. The method can further include a step of calcining at least a portion of hierarchical zeolite composition and contacting the hierarchical zeolite composition with steam. The method can further include a step of impregnating at least a portion of hierarchical zeolite composition with one or more of phosphorous, lanthanum, and manganese.

The zirconium source can be one or more of zirconium chloride, zirconium sulfate, zirconium nitrate, and zirconium oxide. The single template can be a tetra-ammonium salt or hydroxide. The initial zeolite can be one or more of ZSM-5, ZSM-11, ZSM-12, ZSM-23, ZSM-35, ZSM-38 and ZSM-48. In an embodiment, the zirconium source is zirconium chloride and the initial zeolite is ZSM-5.

In an embodiment, the framework modification process includes the steps of contacting the zirconium-substituted zeolite with tetrapropylammonium hydroxide (TPAOH) to produce a TPAOH-treated zeolite; subjecting the TPAOH-treated zeolite to hydrothermal aging; and calcining at least a portion of TPAOH-treated zeolite to produce the framework-modified zeolite. In an embodiment, the ion exchange process includes the steps of contacting the framework-modified zeolite with an acid to produce a hierarchical pore structure in at least a portion of the framework-modified zeolite, resulting in the hierarchical zeolite composition.

In an embodiment, the ion exchange process includes the steps of contacting the framework-modified zeolite with ammonium chloride to produce a hierarchical pore structure in at least a portion of the framework-modified zeolite, resulting in the hierarchical zeolite composition.

Another method of making a hierarchical zeolite composition includes the steps of mixing an alumina source, a silica source, and a zirconium source under reaction conditions to produce a zirconium-containing zeolite; subjecting the zirconium-containing zeolite to a framework modification process using a single template to produce a framework-modified zeolite; and subjecting the framework-modified zeolite to an ion exchange process to produce a hierarchical pore structure in at least a portion of the framework-modified zeolite, resulting in the hierarchical zeolite composition. The method can further include a step of steaming the hierarchical zeolite composition and mixing the hierarchical zeolite with kaolin in a 1:1 ratio to form a slurry containing the hierarchical zeolite and kaolin; stirring the slurry under heat to evaporate water and produce a hierarchical zeolite-kaolin powder mixture; and subjecting the hierarchical zeolite-kaolin powder mixture to calcination.

Embodiments include methods of catalytic cracking of a hydrocarbon-containing feedstock to catalytic cracking conversion products using hierarchical zeolite compositions containing zirconium. One such method includes the steps of providing a hierarchical zeolite composition to a catalytic cracking process and contacting a hydrocarbon-containing feedstock with the hierarchical zeolite composition at catalytic cracking conditions to produce catalytic cracking conversion products. The hierarchical zeolite composition used in this process is prepared by subjecting an initial zeolite and a zirconium source to a partial isomorphous substitution process to produce a zirconium-substituted zeolite; then, subjecting the zirconium-substituted zeolite to a framework modification process using a single template to produce a framework-modified zeolite; and subjecting the framework-modified zeolite to an ion exchange process to produce a hierarchical pore structure in at least a portion of the framework-modified zeolite, resulting in the hierarchical zeolite composition. The zirconium source for this process can be one or more of zirconium chloride, zirconium sulfate, zirconium nitrate, and zirconium oxide. The single template can be a tetra-ammonium salt or hydroxide. The initial zeolite can be one or more of ZSM-5, ZSM-11, ZSM-12, ZSM-23, ZSM-35, ZSM-38 and ZSM-48. In an embodiment, the zirconium source is zirconium chloride and the initial zeolite is ZSM-5.

In certain embodiments, the catalytic cracking conversion products include olefins having 2 to 4 carbon atoms and the yield of these olefins is increased by at least ten percent as compared to yield of these olefins from a catalytic cracking process using the initial zeolite. In certain embodiments, the catalytic cracking conversion products include olefins having 2 to 4 carbon atoms and the yield of these olefins is increased by at least twenty percent as compared to yield of these olefins from a catalytic cracking process using the initial zeolite.

In certain embodiments, the catalytic cracking conversion products include gasoline and yield of the gasoline is decreased by at least ten percent as compared to yield from a catalytic cracking process using the initial zeolite. In certain embodiments, the catalytic cracking conversion products include gasoline and yield of the gasoline is decreased by at least twenty percent as compared to yield from a catalytic cracking process using the initial zeolite.

Catalysts prepared in this manner are better than conventional templated mesoporous zeolites as they encompass zirconium-substituted mesoporous ZSM-5 zeolites that demonstrate improved hydrothermal stability and acidity. Moreover, these mesoporous ZSM-5 zeolite catalytic compositions overcome molecular diffusional limitations that are prevalent in processes, like the down flow HS-FCC. These mesoporous ZSM-5 zeolite catalytic compositions provide more control on the coke formation, and thus, prolong the life of the catalyst. Furthermore, these catalytic compositions can be utilized for catalytic cracking of a paraffinic feedstock into light olefins.

Numerous other aspects, features and benefits of the present disclosure may be made apparent from the following detailed description taken together with the drawings. The systems can include less components, more components, or different components depending on desired goals for the catalytic cracking conversion products.

BRIEF DESCRIPTION OF THE DRAWINGS

While this disclosure is susceptible to various modifications and alternative forms, specific embodiments are shown by way of example in the drawings and will be described in detail here. It should be understood, however, that the drawings and the detailed description are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

Figure 1:
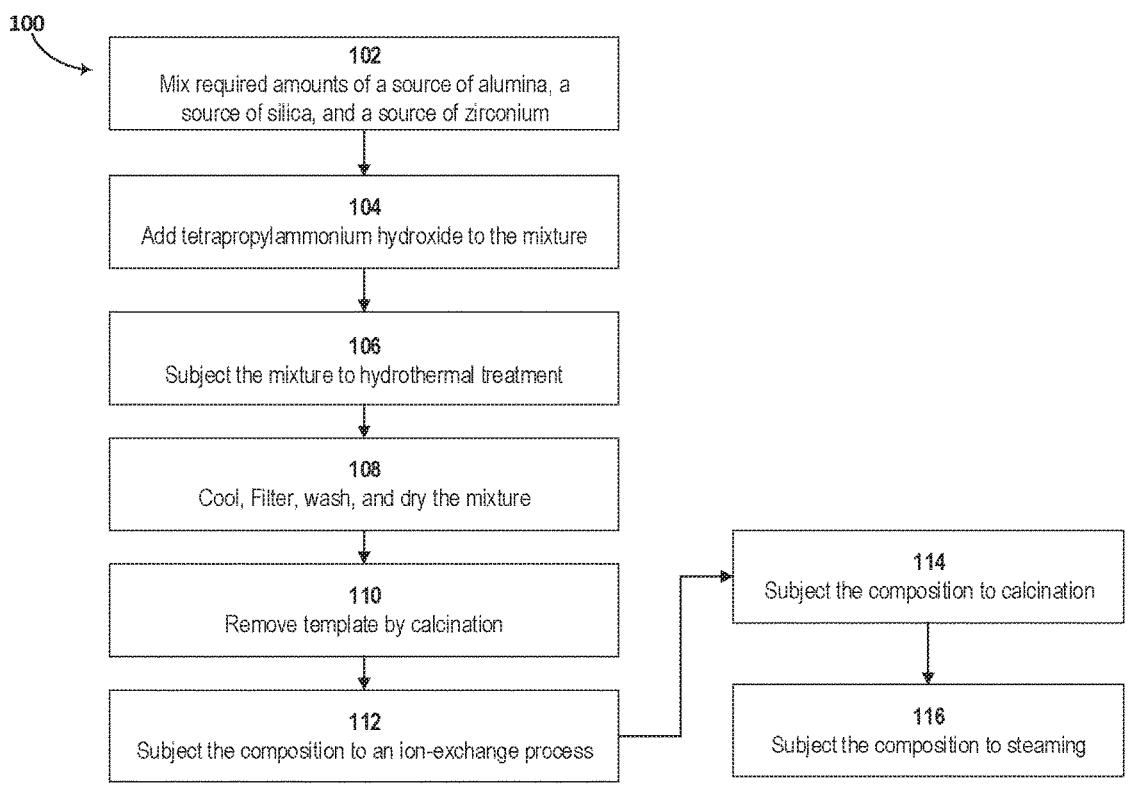
FIG. 1 is a block diagram of a method of making the catalytic composition, according to an embodiment.

In the following description, numerous specific details are set forth in order to provide a thorough understanding of the various embodiments. In other instances, well-known processes and methods may not be described in particular detail in order to not obscure the embodiments described here. Additionally, illustrations of embodiments here may omit certain features or details in order to not obscure the embodiments described here. In the following detailed description, reference is made to the accompanying drawings that form a part of the specification. Other embodiments may be utilized, and logical changes may be made without departing from the scope of the disclosure. The description may use the phrases "in some embodiments," "in various embodiments," "in certain embodiment," or "in embodiments," which may each refer to one or more of the same or different embodiments. Furthermore, the terms "comprising," "including," "having," and the like, as used with respect to embodiments of the present disclosure, are synonymous.

Hierarchical zeolites have a pore structure with more than one level of porosity. Hierarchical zeolites can contain one or more of micropores, mesopores, and macropores. Current processes of generating micro/mesoporous composite catalysts include combination of two different zeolites of different textural characteristics such as acidity and pore structures. Examples of such combinations are ZSM-5/MCM-41, Beta-SBA-15, ZSM-5/ZSM-11, ZSM-5/Y, and ZSM-5/MCM-22 (ZSM stands for Zeolite Socony Mobil, MCM for Mobil Composition of Matter, and SBA for Santa Barbara Amorphous). In order to generate hierarchical porosity, surfactant-based secondary mesoporous templates are used in the art, such as cetyl trimethyl ammonium bromide (CTAB), Pluronic™ triblock polymer F127 (Pluronic™ being a series of poloxamer polymers, available from BASF Corporation, headquartered in Florham Park, N.J.), and Brij™ series of surfactants (polyoxyethylene vegetable-based fatty ethers derived from lauryl, cetyl, stearyl and oleyl alcohols and available from Croda International Plc, headquartered in Snaith, East Riding of Yorkshire, United Kingdom). The surfactant-based templates are not eco-friendly and are expensive.

Embodiments disclosed here are methods of producing hierarchical zeolite catalysts without use of secondary templates. In a partial isomorphous substitution process, at least a portion of the silicon atoms are substituted by another tetravalent element, such as zirconium. Embodiments also include methods of treatment of the hierarchical zeolite catalysts with compounds derived from other IUPAC Group 4 elements, such as titanium and hafnium.

In one such approach, isomorphous substitution of silicon in the ZSM-5 framework by a tetravalent element, such as zirconium, occurs through hydrothermal synthesis. A framework modification process involves using a template to structure the zeolites. While several templates can be used in the process, embodiments include the use of a single template. Then, hierarchical pores are generated through an ion exchange process, such as acid washing. Acids that can be used in this process can be selected from the group consisting of hydrochloric acid, sulfuric acid, nitric acid, acetic acid, sulfonic acid, oxalic acid, citric acid, tartaric acid, malic acid, glutaric acid, succinic acid, and mixtures of two or more of these acids. In certain embodiments, the acids are weak acids. In another embodiment, the pH of the treatment solution is between 4 and 6. The pH of the treatment solution can be 5. The pH of the treatment solution can be 4.95. In certain embodiments, the acids are provided to the reaction in the form of salts. For example, ammonium chloride is provided to the reaction during the ion-exchange step. In certain embodiments, a dilute acidic ammonium chloride solution is used.

As used here, a zirconium-substituted zeolite is a zeolite in which a portion of the silicon atoms forming the zeolite framework is substituted with zirconium atoms. For example, the Zr-ZSM-5 composition is a ZSM-5 composition in which a portion of the silicon atoms forming the ZSM-5 framework is substituted with zirconium atoms. The zirconium-substituted zeolite contains zirconium in the range of 0.1% to 5%, or from 0.2% to 4%, or from 0.3% to 3%, as a weight percentage of zirconium in terms of the total zeolite. The initial zeolite used in synthesis of the zirconium-substituted zeolite can be ZSM-5, ZSM-11, ZSM-12, ZSM-23, ZSM-35, ZSM-38, or ZSM-48. Embodiments also include zeolites substituted with compounds derived from other IUPAC Group 4 elements, such as titanium and hafnium.

Disclosed here are embodiments of methods of preparing hierarchical zeolite compositions. In an embodiment, the method includes the steps of subjecting an initial zeolite and a zirconium source to a partial isomorphous substitution process to produce a zirconium-substituted zeolite, and then, subjecting the zirconium-substituted zeolite to a framework modification process using a single template to produce a framework-modified zeolite. In the next step the framework-modified zeolite is subjected to an ion exchange process to produce a hierarchical zeolite composition containing a hierarchical pore structure in at least a portion of the framework-modified zeolite. This method can further include calcining at least a portion of hierarchical zeolite composition and contacting the hierarchical zeolite composition with steam. In certain embodiments, the partial isomorphous substitution process includes contacting at least a portion of the initial zeolite with a zirconium source, such as one or more of zirconium chloride, zirconium sulfate, zirconium nitrate, and zirconium oxide. The single template can be a tetra-ammonium salt or hydroxide. The single template can be TPAOH. In certain embodiments, the framework modification process includes the steps of contacting the initial zeolite with TPAOH to produce a TPAOH-treated zeolite, followed by subjecting the TPAOH-treated zeolite to hydrothermal aging, and then, calcining at least a portion of TPAOH-treated zeolite to produce the framework-modified zeolite. In certain embodiments, the ion exchange process includes contacting the framework-modified zeolite with an acid to produce the hierarchical zeolite composition containing a hierarchical pore structure in at least a portion of the framework-modified zeolite. In certain embodiments, the ion exchange process includes contacting the framework-modified zeolite specifically with ammonium chloride to produce the hierarchical zeolite composition containing a hierarchical pore structure in at least a portion of the framework-modified zeolite. The initial zeolite can be one or more of ZSM-5, ZSM-11, ZSM-12, ZSM-23, ZSM-35, ZSM-38 and ZSM-48. The hierarchical zeolite composition catalyst can be further impregnated with one or more of phosphorous, lanthanum, and manganese.

Disclosed here are embodiments of methods for synthesizing hierarchical zeolites for efficient cracking of a light petroleum feedstock into value-added products, such as ethylene, propylene, butenes, and aromatics. Addition of transition metals, such as iron and chromium, has been shown to influence the activity and selectivity of zeolites towards light olefins. The presence of even small amounts of iron or chromium was found to favor the dehydrogenation reaction of isobutane to isobutene, which can be easily converted to light olefins. On the other hand, incorporation of some metals, such as silver and zinc, in zeolites was found to enhance aromatics production at the expense of light olefins yield. Therefore, choice of metal to be impregnated into zeolites, the process of making such catalysts, and the reaction conditions play a major role in determining product selectivity.

Disclosed here are embodiments of methods of catalytic cracking of a hydrocarbon-containing feedstock to catalytic cracking conversion products using hierarchical zeolite compositions. In certain embodiments, the method includes the steps of providing a hierarchical zeolite composition to a catalytic cracking process and contacting a hydrocarbon-containing feedstock with the hierarchical zeolite composition at catalytic cracking conditions to produce catalytic cracking conversion products. The hierarchical zeolite composition is prepared by subjecting an initial zeolite to a partial isomorphous substitution process to produce a zirconium-substituted zeolite, followed by subjecting the zirconium-substituted zeolite to a framework modification process using a single template to produce a framework-modified zeolite, and then, subjecting the framework-modified zeolite to an ion exchange process to produce a hierarchical zeolite composition containing a hierarchical pore structure in at least a portion of the framework-modified zeolite. The initial zeolite can be one or more of ZSM-5, ZSM-11, ZSM-12, ZSM-23, ZSM-35, ZSM-38 and ZSM-48. The hierarchical zeolite composition can be further impregnated with one or more of phosphorous, lanthanum, and manganese. The preparation of the hierarchical zeolite composition can also include calcining at least a portion of hierarchical zeolite composition and contacting the hierarchical zeolite composition with steam, before contacting the hierarchical zeolite composition with the hydrocarbon-containing feedstock.

In certain embodiments, petroleum feedstocks, such as Khuff Gas Condensate (KGC), are used as starting materials. Feeds like KGC have attractive properties in terms of low sulfur, nitrogen, metals and Conradson carbon. These feeds could be potential feedstocks for the FCC process in general and the HS-FCC technology in particular. Certain embodiments of KGC feedstock contain 65% paraffins, 21% naphthenes, and 15% aromatics, along with negligible amounts of olefins. A negligible amount of olefins means olefins may be present in the KGC feedstock, but is present at an amount below the threshold of detectability by a PONA (paraffins, olefins, naphthenes, and aromatics content) analysis. In certain PONA analysis, gas chromatography is utilized to determine the paraffin, olefin, naphthene, and aromatic compositions of complex hydrocarbon mixtures.

The catalytic cracking conversion products include gasoline, hydrogen, methane, ethane, ethylene, propane, propylene, isobutene, n-butane, and plurality of C4 olefins, such as trans but-2-ene, but-1-ene, isobutylene, cis but-2-ene, and 1,3-butadiene. Other compounds present in the catalytic cracking system include light cycle oil, heavy cycle oil, and coke. In some embodiments, the catalytic cracking conversion products include olefins having 2 to 4 carbon atoms and yield of such olefins is increased by at least five percent as compared to yield of such olefins from a catalytic cracking process using the initial zeolite without the zirconium. In some embodiments, the yield of such olefins is increased by at least ten percent as compared to yield of such olefins from a catalytic cracking process using the initial zeolite without the zirconium. In some embodiments, the yield of such olefins is increased by at least twenty percent as compared to yield of such olefins from a catalytic cracking process using the initial zeolite without the zirconium. In some embodiments, the yield of such olefins is increased by at least thirty percent as compared to yield of such olefins from a catalytic cracking process using the initial zeolite without the zirconium. In some embodiments, the catalytic cracking conversion products include gasoline and yield of the gasoline is decreased by at least five percent as compared to yield from a catalytic cracking process using the initial zeolite. In some embodiments, the yield of the gasoline is decreased by at least ten percent as compared to yield from a catalytic cracking process using the initial zeolite. In some embodiments, the yield of the gasoline is decreased by at least twenty percent as compared to yield from a catalytic cracking process using the initial zeolite.

Disclosed here are embodiments of methods for treatment of KGC over hierarchical zeolites-based FCC catalysts. In certain embodiments, the hierarchical zeolites-based FCC catalysts are ZSM-5 zeolites impregnated with zirconium and used in the HS-FCC reactions. These reactions can be carried out in down flow reactor systems.

Cracking activity depends both on acidity of zeolites and on their pore size distribution. The metal-substituted mesoporous zeolites are robust catalysts with improved hydrothermal stability and acidity. The insertion of a labile metal component, such as zirconium, was carried using in situ hydrothermal aging and mesopores were generated using a mild acid treatment. The hierarchical pore structure was composed of micropores and mesopores. In certain embodiments, the hierarchical pore structure also included macropores. The pore size distribution of ZSM-5 was 2.5 nanometers. After modification, the mesopores in the metal-substituted zeolite compositions have a pore diameter ranging from 2 to 4 nanometers with mesopore volume ranging from 0.26 cubic centimeters per gram (cc/g or $cm^3/g$). Additionally, the macropores in the metal-substituted zeolite compositions can have a pore diameter ranging from 50 to 130 nanometers. The mesopore size distribution of these catalytic compositions comprised both ordered and disordered pore structures. The mesopores were disordered, but the pore diameters could be uniformly tailored. The hierarchical pores with non-uniform pore size distribution are derived by introduction of zirconium species in the ZSM-5 framework.

The ordered/disordered pores were formed through a demetallation process using acid treatment and steaming. An example of the steaming treatment includes use of saturated steam at temperatures ranging from 700-850° C. for three hours. Methods also include desilication and templating, or templating and steaming. Other embodiments include the hierarchical modification being carried out using steaming alone, templating techniques (cetyl trimethyl ammonium bromide) alone, dealumination alone, and desilication alone. These methods of making the metal-substituted zeolite compositions are reproducible and scalable.

The synthesized zirconium-containing zeolites had crystalline frameworks with a greater number of acidic sites as compared to ZSM-5 compositions without the zirconium. The performance of the new hierarchical catalyst compositions was found to maximize the light olefin yields from the cracking of several light and heavy petroleum feedstocks using the FCC process. In an embodiment, the feedstock supplied to a HS-FCC reaction is KGC feedstock. The synthesized catalysts were very efficient for the cracking of KGC into light olefins, specifically propylene.

In an embodiment of a method of making the catalytic composition, zirconium is introduced inside the framework of ZSM-5 through isomorphous substitution, and only one template—TPAOH is used. Other compounds that can be used as single templates in the process include tetrabutylammonium hydroxide, N,N-dimethylformamide, trimethylcetylammonium hydroxide, diaminoethane, and ammonium hydroxide. In this method, ion-exchange is implemented to transform aluminates from the Na-form to the H-form, which creates mesoporosity. The zirconium inside the framework of the zeolite is partially removed using dilute acidic solutions, such as a 1 M ammonium chloride ($NH_4Cl$) solution. This one-template synthesis method is advantageous, as it avoids the use of excessive templating. This method avoids the use of fluoride-based components and alkaline solutions. Thus, this method is eco-friendly and easily upgraded to industrial scale synthesis. In certain embodiments, the final product is a single-phased zirconium containing ZSM-5.

Other embodiments of a method of making a hierarchical zeolite composition include the steps of mixing an alumina source, a silica source, and a zirconium source under reaction conditions to produce a zirconium-containing zeolite, followed by subjecting the zirconium-containing zeolite to a framework modification process using a single template to produce a framework-modified zeolite, and then, subjecting the framework-modified zeolite to an ion exchange process to produce a hierarchical pore structure in at least a portion of the framework-modified zeolite, resulting in the hierarchical zeolite composition. The single template can be a tetra-ammonium salt or hydroxide. The single template can be TPAOH. The method can further include a step of steaming the hierarchical zeolite composition and mixing the hierarchical zeolite with kaolin in a 1:1 ratio to form a slurry containing the hierarchical zeolite and kaolin; stirring the slurry under heat to evaporate water and produce a hierarchical zeolite-kaolin powder mixture; and subjecting the hierarchical zeolite-kaolin powder mixture to calcination. FIG. 1 is a block diagram of a method 100 of making the catalytic composition according to an embodiment. The required amounts of a source of alumina (such as sodium aluminate), a source of silica (such as Ludox® AS-40 colloidal silica available from Millipore Sigma headquartered in Billerica, Mass., United States), and a source of zirconium (such as zirconium tetrachloride) were mixed, as in step 102. In some embodiments, the source of zirconium can be added to a zeolite composition. Other sources of zirconium include one or more of zirconium sulfate, zirconium nitrate, and zirconium oxide. In certain embodiments, the mole ratio of an oxide source of silica and an oxide source of alumina ranges from 100 to 250 and the mole ratio of an oxide source of silica and an oxide source of zirconium ranges from 20 to 250. TPAOH is then added to the mixture containing the zirconium-substituted zeolite, as in step 104. The resulting mixture was stirred at room temperature for 24 hours. As part of the framework modification process, the mixture was then subjected, as in step 106, to hydrothermal treatment. An example of hydrothermal treatment involves injection of saturated steam of 150-200° C. into the reactor containing the zirconium-substituted zeolites, for three days with rotation (70 rpm) under autogenous pressure conditions. The mixture was cooled down, filtered, washed and dried at 100° C. overnight, as in step 108. The template was removed by calcination at 600° C. for 10 hours with heating rate of 2 degrees Celsius per minute (° C./min), as in step 110. The framework-modified zeolites were then subjected to an ion-exchange process, such as an acid wash with 1M $NH_4Cl$ solution, as in step 112, and then calcined to generate the proton form at 500° C. for 2 hours, as in step 114. In certain embodiments, the sample are calcined at temperatures, ranging from 500° C. to 800° C. and for extended periods beyond two hours, such as 3 to 8 hours. The rate of heating can range from a rate of 1 to 5° C./min. The calcined hierarchical Zr-ZSM-5 composition is then exposed to steam, as in step 116. The steaming process was performed using 100% steam at temperatures ranging from 700° C.-850° C. for three hours.

The removal of zirconium from the framework after ion-exchange was confirmed through inductively coupled plasma atomic emission spectroscopy (ICP analysis). In an embodiment, the molar ratio of hierarchical Zr-ZSM-5 before ion-exchange of $SiO_2/Al_2O_3$ was 91 and $SiO_2/ZrO_2$ was 38. The molar ratio of hierarchical Zr-ZSM-5 after ion-exchange of $SiO_2/Al_2O_3$ was 86 and $SiO_2/ZrO_2$ was 42. The $SiO_2/Al_2O_3$ decreased while $SiO_2/ZrO_2$ increased; thus, confirming the removal of zirconium species from the ZSM-5 framework. The calcined hierarchical Zr-ZSM-S can be further impregnated with phosphorus, or lanthanum, or manganese oxides. The weight of phosphorus, or lanthanum, or manganese oxides that can impregnate the calcined hierarchical Zr-ZSM-5 can range from 2 to 5 weight percent (wt %) of the calcined hierarchical Zr-ZSM-5 composition.

In certain embodiments, the steamed zeolites were mixed with kaolin in a 1:1 ratio. Under laboratory conditions, a known volume of water was taken in a petri dish and kaolin was added slowly while stirring. This kaolin slurry was stirred well to obtain a homogeneous mixture. The required amount of zeolite composition was added slowly to this kaolin-water mixture while being continuously stirred. The zeolite-kaolin-water slurry was thoroughly mixed to obtain a homogeneous slurry. This slurry was heated slowly to 90° C. to evaporate the water. The zeolite-kaolin powder mixture was further calcined at 550° C. prior to microactivity testing.

Figure 2:
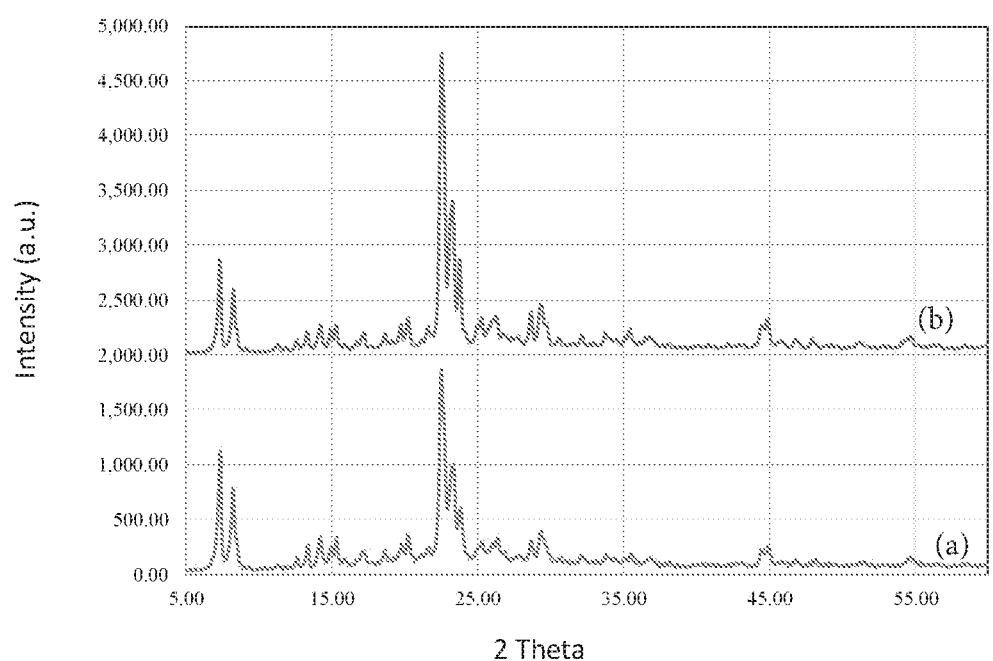
FIG. 2 presents the x-ray diffraction (XRD) patterns for hierarchical ZSM-5 with zirconium (line (a)) and conventional ZSM-5 without zirconium in the framework (line (b)), according to an embodiment.

FIG. 2 presents the XRD patterns for hierarchical ZSM-5 with zirconium (line (a)) and conventional ZSM-5 without zirconium in the framework (line (b)), prepared according to an embodiment. The XRD patterns are representative of typical mordenite framework inverted (MFI) structures. The two diffraction patterns are presented on the same intensity scale, but are presented offset for clarity. As evident from FIG. 2, there is an intensity difference between conventional ZSM-5 and Zr-ZSM-5. Substitution of zirconium did not alter the crystal structure. Increased d spacing from 20 to 22.6 confirms that zirconium was substituted isomorphously.

Figure 3:
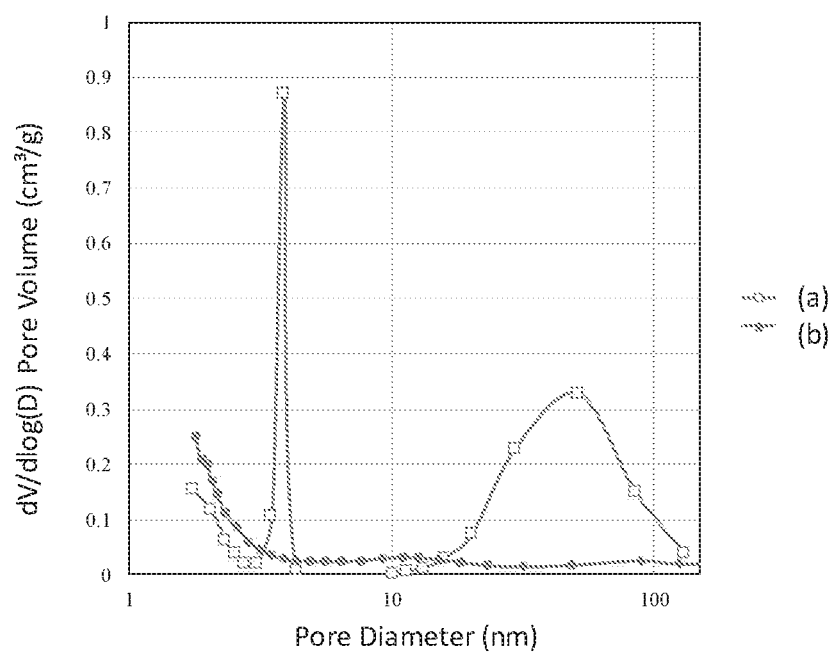
FIG. 3 is a Barrett-Joyner-Halenda (BJH) analysis plot of pore size distribution against pore diameter of the ion-exchanged Zr-ZSM-5 (line (a)) and ZSM-5 (line (b)), according to an embodiment.

The structure of the pores was characterized using the nitrogen ($N_2$) adsorption/desorption isotherms, which were obtained using an automated surface area analyzer. The pore volume versus diameter distribution was calculated by analyzing both the adsorption and desorption branches of the isotherm using the Barrett-Joyner-Halenda (BJH) method. The BET surface area and pore structure of the calcined catalysts were measured on a Micromeritics ASAP 2020 instrument (available from Micromeritics Instrument Corporation, headquartered at Norcross, Ga., USA). Before adsorption measurements, about 0.1 gram of samples were degassed at 240° C. for 3 hours under nitrogen flow. The nitrogen adsorption isotherms were measured at liquid nitrogen temperature (−196° C.). FIG. 3 is a BJH analysis plot of the logarithmic differential pore volume distribution against pore diameter of the ion-exchanged Zr-ZSM-5 and ZSM-5, respectively, prepared according to an embodiment. As shown by line (a) in FIG. 3, hierarchical Zr-ZSM-5 displayed greater pore volume arising from the contribution of both mesopores and macropores formation after ion-exchange. The zirconium incorporation appears to have changed the textural character of ZSM-5. The ion exchange process using mild acid conditions results in the generation of the mesopores and macropores. The ZSM-5 without zirconium in the framework shows no hierarchical pore formation after ion exchange, as shown by line (b) in FIG. 3. There is no macropore formation in the ZSM-5 sample as compared to Zr-ZSM-5 sample. The formation of mesopores and macropores following ion exchange using 1 M $NH_4Cl$ solution was observed, and thus, confirming the new approach for generation of hierarchicity without using expensive, non-ecofriendly secondary template. Moreover, when the crystal size of the zeolites is close to the molecular diameter of light hydrocarbons, the diffusion of the reactant/product molecules within pores in the catalyst is usually the rate-limiting step of the reaction. Furthermore, coke formation on the crystal surface is favored under diffusion-controlled regime, which obstructs the accessibility of the pores and thus deactivates the catalyst. The hierarchical ZSM-5 catalysts with zirconium prepared as disclosed here do not suffer from these drawbacks.

Figure 4:
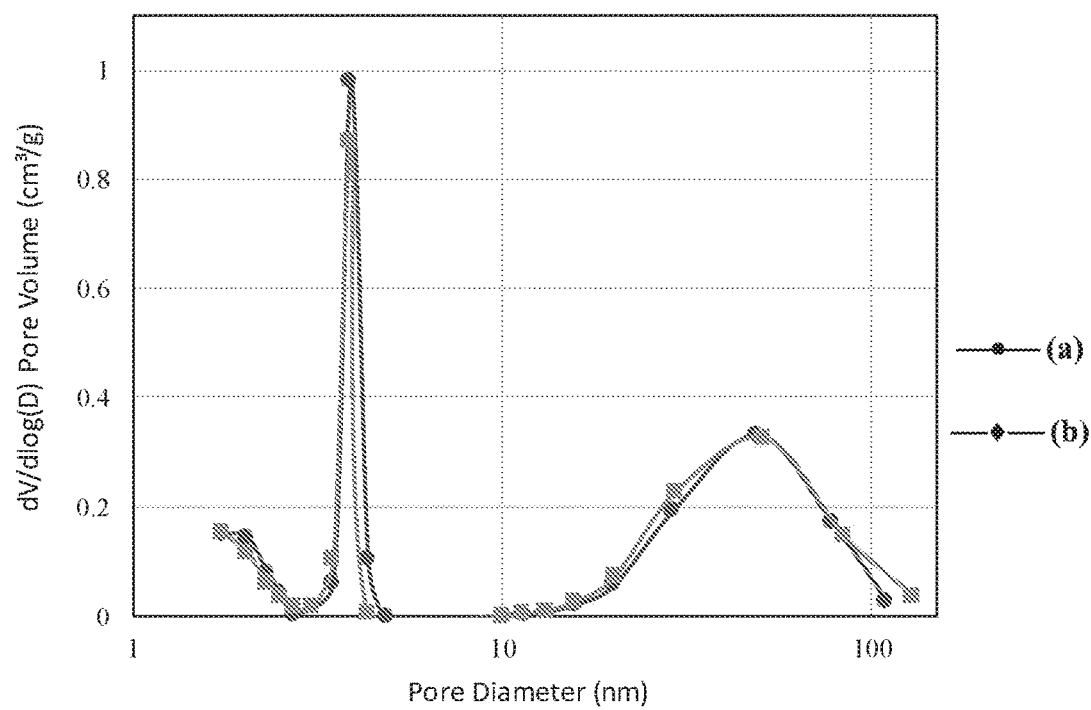
FIG. 4 is a BJH analysis plot of pore size distribution against pore diameter of the ion-exchanged Zr-ZSM-5 without being subject to steaming (line (a)) and ion-exchanged Zr-ZSM-5 subject to steaming (line (b)), according to an embodiment.

The steaming conditions are set so that the steamed catalyst has properties similar to the catalysts used in commercial FCC units. Prior to testing, all the fresh catalysts were subjected to hydrothermal deactivation treatment according to ASTM method D 4463, titled "Standard Guide for Metals Free Steam Deactivation of Fresh Fluid Cracking Catalysts." Catalysts that were subsequently evaluated using KGC as the feedstock were steamed at 750° C. for three hours. FIG. 4 is a BJH analysis plot of the logarithmic differential pore volume distribution against pore diameter of the ion-exchanged Zr-ZSM-5 without being subject to steaming (as shown by line (a)) and ion-exchanged Zr-ZSM-5 subject to steaming (as shown by line (b)). Steaming did not affect the differential pore volume distribution of the Zr-ZSM-5 when plotted against its pore diameter. This BJH analysis demonstrated that the generated mesopores and macropores were stable at steaming conditions of 750° C. for at least three hours.

Figure 5A:
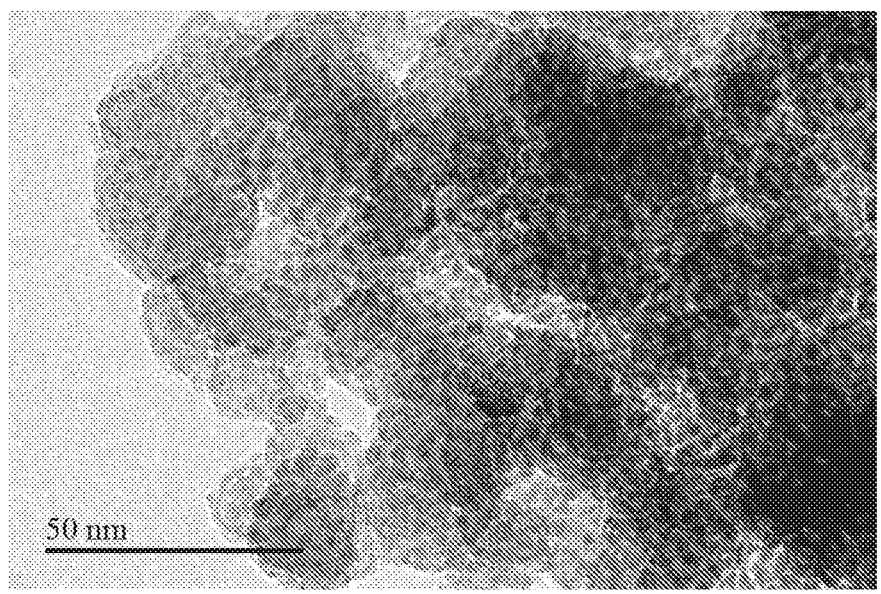
FIGS. 5A and 5B are images obtained by transmission electron microscopy (TEM) of hierarchical ZSM-5 with zirconium and conventional ZSM-5 without zirconium in the framework, respectively, according to an embodiment.
Figure 5B:
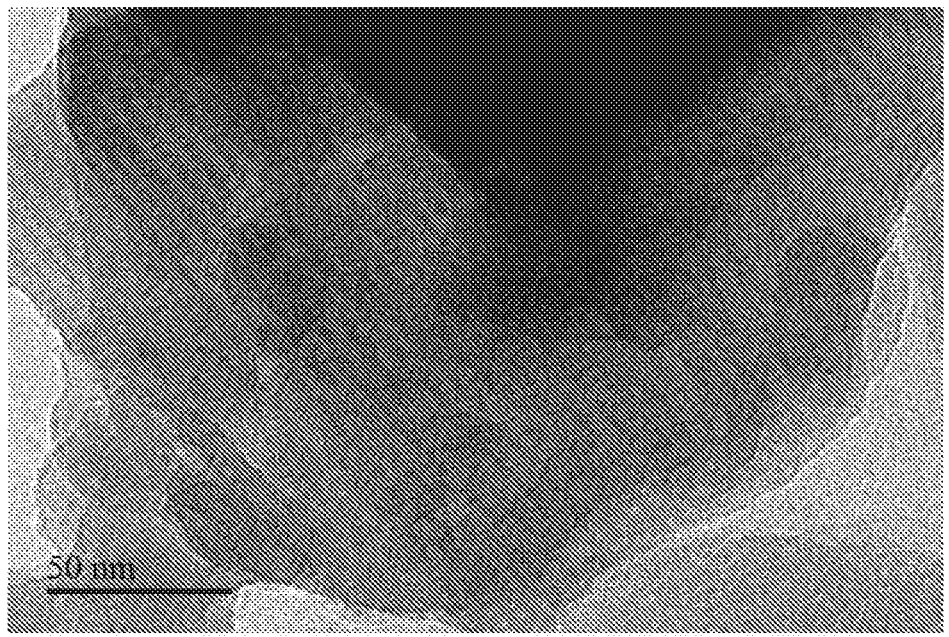

The ZSM-5 catalyst was subject to the ion-exchange process under the same conditions as the Zr-ZSM-5 catalyst. FIGS. 5A and 5B are TEM images at a resolving magnification of 50 nm of hierarchical ZSM-5 with zirconium and conventional ZSM-5 without zirconium in the framework, respectively, according to an embodiment. The morphologies of the calcined catalysts were characterized by an advanced field emission transmission electron microscope (HRTEM-model JEM-2100F, available from JEOL USA, Inc., with headquarters at Peabody, Mass., USA) with an acceleration voltage of 200 kilovolts. The high-resolution images have been obtained on a charge coupled-device (CCD) camera and crystallographic information of oxide layers were obtained using Fast Fourier Transform technique. As seen in FIGS. 5A and 5B, the orderedness of the pore structure was retained and ion-exchange had little impact on the structure of the hierarchical ZSM-5 with zirconium. This observation is in alignment with the expected stability of ZSM-5. In Zr-ZSM-5, zirconium is regularly distributed as nanosized zirconium species. The generation of hierarchical pores are clearly visible after acid treatment using 1M $NH_4Cl$ solution (FIG. 5A).

Figure 6:
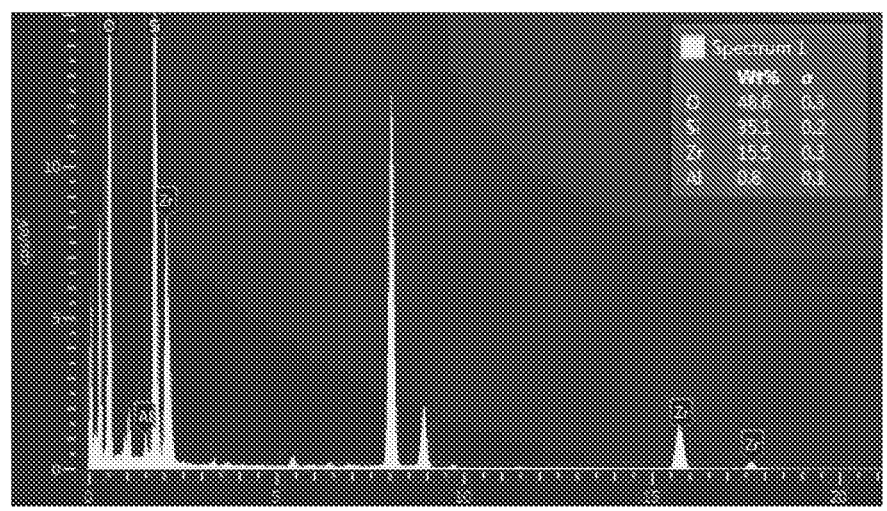
FIG. 6 is the energy-dispersive X-ray spectroscopy (EDS) spectrum of the hierarchical Zr-ZSM-5 composition having a mordenite framework inverted (MFI) structure, according to an embodiment.

The hierarchical Zr-ZSM-5 composition was subjected to EDS for elemental analysis. The morphological characterization and elemental composition of the catalyst was carried on a JEOL JSM 5600LV Scanning Electron Microscope (available from JEOL USA, Inc. with headquarters at Peabody, Mass., USA) coupled with an EDS analyzer for compositional analysis. FIG. 6 is the EDS spectrum of the Zr-ZSM-5 composition having an ordered MFI structure. The EDS spectrum shows the presence of zirconium in addition to aluminum and silicon in the Zr-ZSM-5 composition. The multiple zirconium peaks show the excitation of electron from inner shell of Zr atoms and electron filling from different outer greater energy shells of the Zr atoms. Also provided is an inset showing the concentration in weight percent of each of the elements—oxygen, silicon, aluminum, and zirconium—in the Zr-ZSM-5 composition and the error in the weight percent concentration at the one sigma ($1\sigma$) level.

Figure 7:
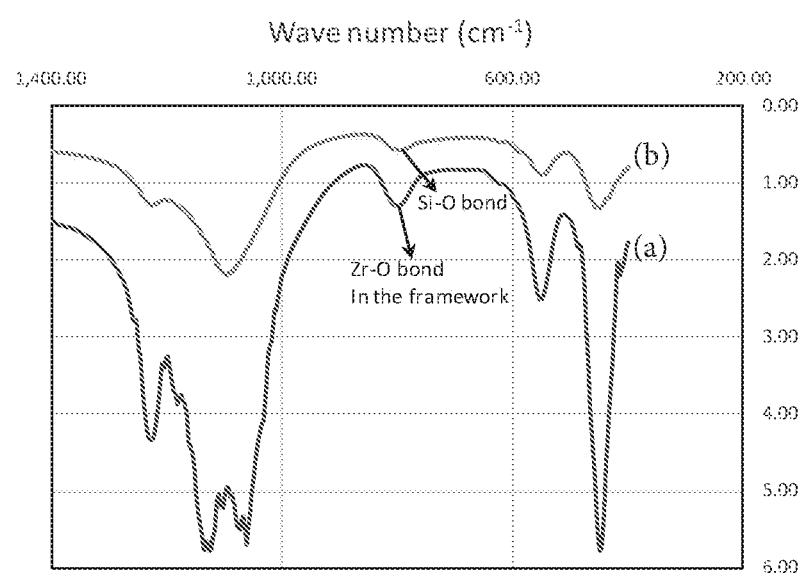
FIG. 7 is the infrared spectra for hierarchical ZSM-5 with zirconium (spectrum (a)) and conventional ZSM-5 without zirconium in the framework (spectrum (b)), according to an embodiment.

The hierarchical ZSM-5 with zirconium and conventional ZSM-5 without zirconium were subject to Fourier-transform infrared spectroscopy (FTIR). The FTIR spectra was recorded using Nicolet Avatar spectrometer (available from Thermo Nicolet Corporation with headquarters at Madison, Wis., USA) and the potassium bromide (KBr) pellet technique. About 3 milligrams (mg) of a zeolite sample was grounded with 100 mg of KBr to form a thoroughly mixed preparation that was then pelletized to record in the 4000-400 reciprocal centimeter ($cm^{-1}$) range. FIG. 7 presents the infrared spectrum for conventional ZSM-5 without zirconium in the framework (spectrum (a)) and hierarchical ZSM-5 with zirconium (spectrum (b)). The framework infrared spectrum of Al-ZSM-5 and Zr—Al-ZSM-5 were recorded between 400 and 1200 $cm^{-1}$. The existence of strong absorption between 740 and 840 $cm^{-1}$ shows the existence of Zr-O bond in a transition metal tetraoxide tetrahedron, namely the presence of $ZrO_2$ tetrahedron in the framework of hierarchical Zr-ZSM-S.

Figure 8:
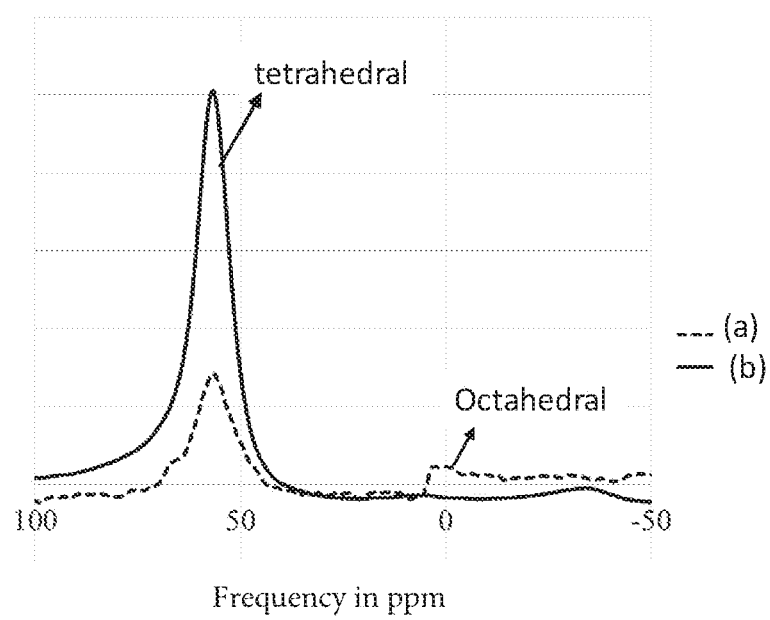
FIG. 8 is the $^{27}Al$ magic-angle spinning (MAS) nuclear magnetic resonance (NMR) spectrum for hierarchical ZSM-5 with zirconium (spectrum (a)) and conventional ZSM-5 without zirconium in the framework (spectrum (b)), according to an embodiment.

The hierarchical ZSM-5 with zirconium and conventional ZSM-5 without zirconium were subject to $^{27}Al$ magic-angle spinning (MAS) nuclear magnetic resonance (NMR) spectroscopy to understand structural details. The $^{27}Al$ MAS NMR spectra was recorded using a JEOL' ECA 600 spectrometer (available from JEOL Ltd. with headquarters at Akishima, Tokyo, Japan) and equipped with a 4-millimeter zirconia rotor. The spin rate was maintained at 15 kilohertz at resonance frequency 156.4 megahertz. FIG. 8 presents the $^{27}Al$ MAS NMR spectrum for hierarchical ZSM-5 with zirconium (spectrum (a)) and conventional ZSM-5 without zirconium in the framework (spectrum (b)). The NMR signal is plotted on the y-axis and the proton resonance frequency in parts per million (ppm) is plotted on the x-axis. The $^{27}Al$ MAS NMR spectra (a) of the Zr-ZSM-5 showed a stronger resonance at approximately 50 ppm assigned to tetrahedral Al-sites compared to $^{27}Al$ MAS NMR spectra (b) of the ZSM-5. And, the $^{27}Al$ MAS NMR spectra of the Zr-ZSM-5 showed a weaker signal at approximately 0 ppm due to hexacoordinated Al-sites. This shows the competitiveness for Zr and Al led to considerable reconstruction of framework tetrahedral Al sites.

Figure 9:
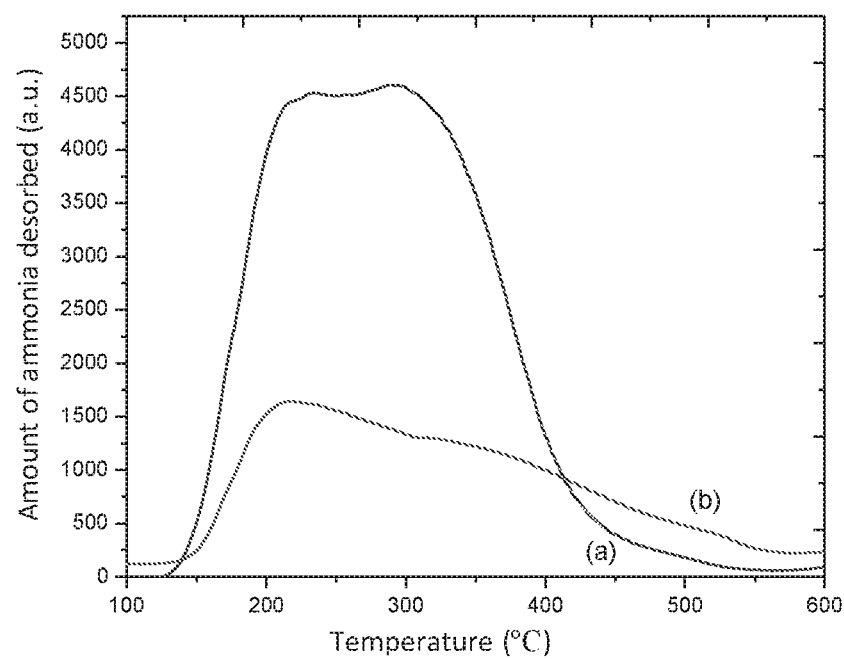
FIG. 9 is the temperature programmed desorption (TPD) profile for hierarchical ZSM-5 with zirconium (a) and conventional ZSM-5 without zirconium in the framework (b), according to an embodiment.

The hierarchical ZSM-5 with zirconium and conventional ZSM-5 without zirconium were subject to temperature programmed desorption (TPD) to observe desorbed molecules from a surface when the surface temperature is increased. The TPD of ammonia is used to reveal the acidic property of zeolites. The TPD profiles for ammonia desorption are obtained by saturation of the surface of the sample with ammonia under set adsorption conditions, followed by linear ramping of the temperature of the sample at a specific heating rate in a flowing inert gas stream. TPD analysis was carried out in BELCAT-A® 200 chemisorption instrument (available from BEL Japan, Inc. with headquarters in Osaka, Japan). The equipment consists of quartz sample holder with a high temperature furnace, and a pair of a thermal conductivity detector (TCD) and a mass spectrometer. The calcined catalyst sample (100 mg) was pretreated regularly in a flow of helium gas (50 milliters per minute (mL/min)) at 500° C. for 1 hour. Then the sample was exposed to a mixture of helium and ammonia (95/5 vol %) at 100° C. for 30 minutes. The gas phase ammonia was removed by helium purging for 1 hour followed by TPD, which was performed in a helium flow (50 mL/min) at a heating rate of 10° C./min, and the desorbed ammonia was monitored by either a TCD detector or a mass spectroscopy. FIG. 9 presents the TPD profile for hierarchical ZSM-5 with zirconium (line (a)) and conventional ZSM-5 without zirconium in the framework (line (b)). The TPD profile (a) of hierarchical Zr-ZSM-5 shows the presence of medium acid sites, as indicated by the TPD signal between approximately 200° C. and 350° C. The broad and larger peak of TPD profile (a) shows the increase in total acidity of the Zr-ZSM-5 composition, the presence of different type of acid sites, and dispersion influences of active sites. The deconvolution shows the presence of two distinct peaks between 200-400° C. The peak around 220° C. shows the presence of weak acid sites due to well dispersed Zr=O species, while peak around 300° C. shows the presence of strong acid sites due to incorporated Zr ions. The TPD ammonia profile (b) of ZSM-5 shows the presence of both medium and strong acid sites, as indicated by the TPD signals at approximately 200° C. and 400° C., but a decrease in total acidity.

Figure 10A:
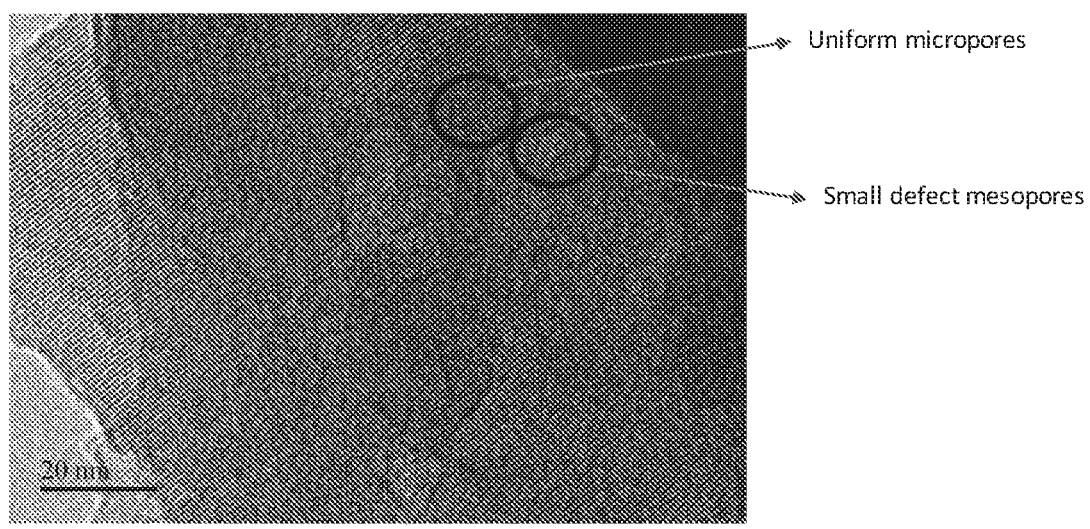
FIGS. 10A and 10B are TEM images at a resolving magnification of 20 nanometers (nm) of conventional ZSM-5 without zirconium and hierarchical ZSM-5 with zirconium in the framework, respectively, according to an embodiment.
Figure 10B:
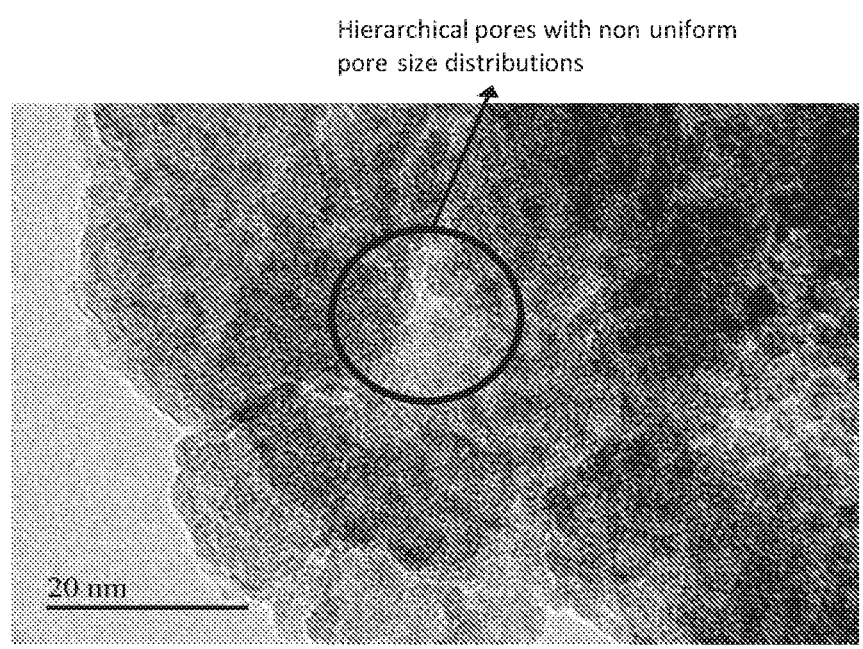

The mesopore size distribution of these catalytic compositions comprised both ordered and disordered pore structures. The mesopores were disordered, but the pore diameters could be uniformly tailored. FIGS. 10A and 10B are TEM images at a resolving magnification of 20 nm of hierarchical ZSM-5 without zirconium and conventional ZSM-5 with zirconium in the framework, respectively. In case of conventional ZSM-5, micropores are retained in major proportion, while some defects as mesopores are created, as evident from the TEM image presented in FIG. 10A. In the case of Zr-ZSM-5 compositions, hierarchical pores are distinctly generated after ion exchanging process under mild acidic environment, as evident from the TEM image presented in FIG. 10B.

Figure 11:
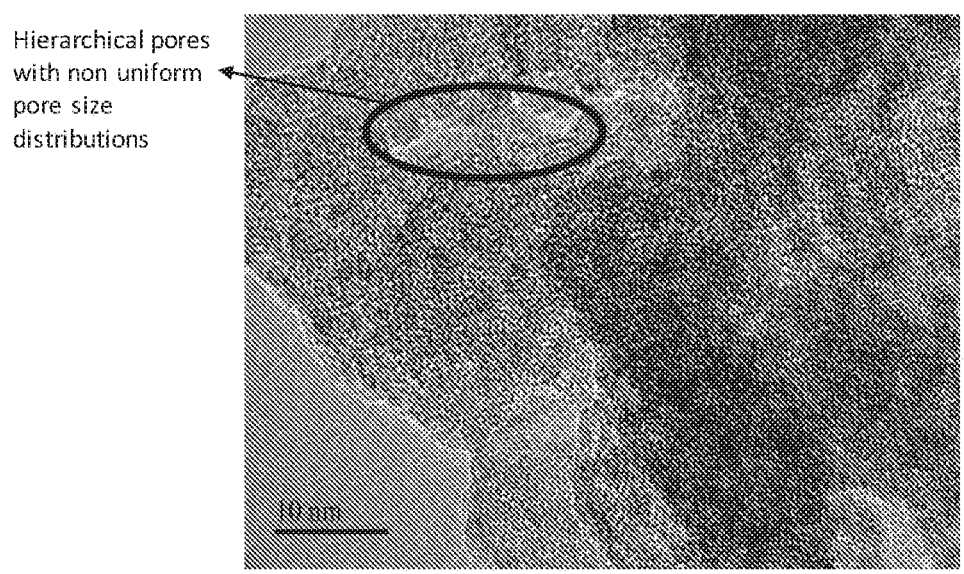
FIG. 11 is a TEM image of hierarchical ZSM-5 with zirconium in the framework at a resolving magnification of 10 nm, according to an embodiment.
Figure 12:
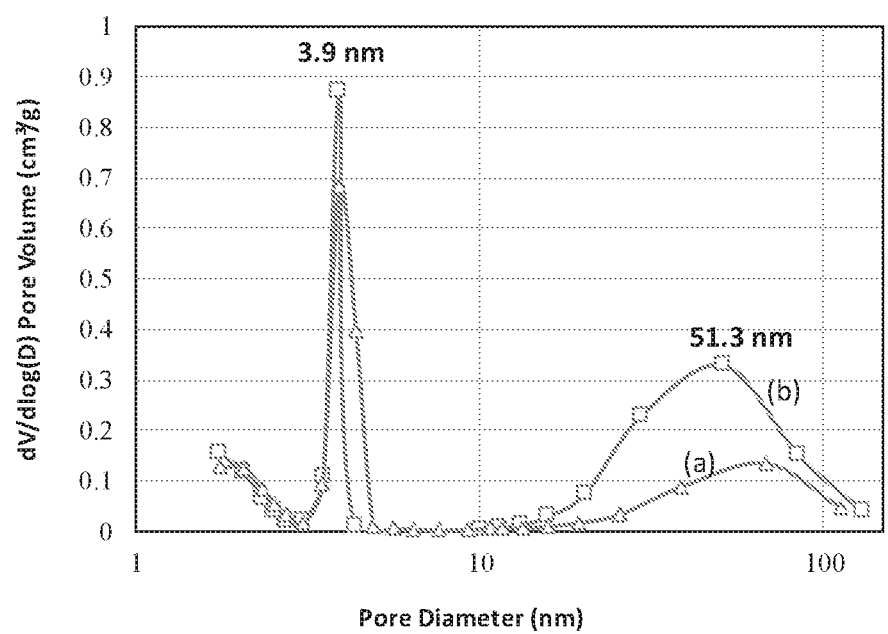
FIG. 12 is a BJH analysis plot of pore size distribution against pore diameter of the calcined Zr-ZSM-5 sample before (line (a)) and after ion-exchange process (line (a)), according to an embodiment.

FIG. 11 is a TEM image at a resolving magnification of 10 nm of hierarchical ZSM-5 with zirconium in the framework. The hierarchical pores with non-uniform pore size distribution due to presence of zirconium species in the ZSM-5 framework are evident in FIG. 11. The nature of pore size distribution was evaluated through surface area measurement. FIG. 12 is a BJH analysis plot of the logarithmic differential pore volume distribution against pore diameter of the calcined Zr-ZSM-5 sample before and after ion-exchange process, respectively, according to an embodiment. The ion-exchange treatment creates pores of ordered and disordered distributions. The pore size distribution curves of the compositions following typical calcination before ion-exchange (line (a)) and calcination after ion-exchange (line (b)) reveals the biporosity enhancement from ordered meso to disordered macropores.

The following Examples are set forth to aid in understanding various embodiments, and are not intended and should not be construed in any way to limit the disclosure to particular embodiments.

Example 1

The catalysts were evaluated in a fixed-bed micro activity test (MAT) unit (available from Sakuragi Rikagaku, Japan), using a quartz tubular reactor. The synthesized catalysts were evaluated for cracking KGC according to ASTM D-3907 method, titled "Standard Test Method for Testing Fluid Catalytic Cracking (FCC) Catalysts by Microactivity Test." All catalysts were steamed at 750° C. for 3 hours prior to the reaction. The experiments were conducted in the MAT unit at 30 second time-on-stream. The reactor was charged with a known amount of catalyst and approximately 1 gram (g) of KGC feedstock was then fed to the reactor along with 30 mL/min of $N_2$ flow. After each reaction, catalysts were stripped using a $N_2$ stream at 30 mL/min for 5 min. During the reaction and stripping modes, any liquid and gaseous products were collected and subject to a gas chromatographic analysis. The spent catalysts were used to measure the amount of generated coke from the reaction.

The main properties of the KGC sample are shown in Table 1. Sulfur was measured in parts per million (ppm) by mass, while the metals were measured in parts per billion (ppb) by mass.

TABLE 1

| Property | Value |
| --- | --- |
| Density at 15° C., grams per cubic centimeter | 0.7695 |
| Micro carbon residue, wt % | 0.03 |

TABLE 1-continued

| Property | Value |
| --- | --- |
| Sulfur, ppm | 271 |
| Hydrogen content, wt % | 14.1 |
| Vanadium, ppb | <20 |
| Nickel, ppb | <20 |
| Iron, ppb | <20 |

This sample was subjected to PONA analysis, which is the analysis of hydrocarbon mixtures by separation and quantitation of fractions according to the carbon number or type of hydrocarbon. The results of the PONA analysis of this sample are shown in Table 2. There is negligible olefin content in this KGC sample.

TABLE 2

| PONA Analysis | Weight % |
| --- | --- |
| Paraffins | 63.9 |
| Olefins | 0 |
| Naphthenes | 21.3 |
| Aromatics | 14.8 |

This sample was subjected to true boiling point (TBP) analysis, which is a standard batch distillation test used to determine the quality of components by determining the distribution range of the boiling points of the individual components. The distillation-based analysis shows the cumulative weight percent (wt %) of components that fractionate from the KGC sample at the specific temperatures. The results of the TBP analysis of this sample are shown in Table 3.

TABLE 3

| TBP analysis (wt %) | ° C. |
| --- | --- |
| 5 | 24 |
| 10 | 57 |
| 30 | 112 |
| 50 | 163 |
| 80 | 273 |
| Final boiling point | 478 |

To establish a base case, a catalyst was prepared using conventional ZSM-5 ($SiO_2/Al_2O_3$ ratio of 100 and $SiO_2/ZrO_2$ ratio of 0 (without zirconium in the framework)). This ZSM-5 catalyst was mixed with kaolin in a weight ratio of 1:1 before being provided to the MAT analysis. The ratio of catalyst mass to feed mass is referred to as the catalyst/oil ratio and typically ranges from 3 to 10. The ZSM-5 catalyst was tested in a fixed-bed micro-activity flow reactor at 650° C. and a feed injection time of 30 seconds using KGC feed and a catalyst/oil ratio of 8.1. A gas chromatographic analysis of all MAT products was performed to quantify light hydrocarbons up to C4, heavy products (light cycle oil and heavy cycle oil), and gaseous components. After gas analysis, the weight of each gas component was added and the weight of all gas components heavier than C4 was added to the gasoline fraction. Coke on spent catalyst was determined by Horiba Carbon-Sulfur Analyzer Model EMIA-220 V. All results are presented as weight percent (wt %) of the product. The conversion of KGC feeds is defined as the total yield of the hydrocarbons from C1 to C4, gasoline, heavy products, and coke, and was approximately 87.63%. The yields of the various individual components are presented in Table 4.

TABLE 4

| Yields | (wt %) |
|---|---|
| $H_2$ | 0.34 |
| Methane (C1) | 2.96 |
| Ethane (C2) | 2.37 |
| Ethylene (C2=) | 8.12 |
| Propane (C3) | 2.37 |
| Propylene (C3=) | 14.83 |
| Isobutene (iC4) | 0.74 |
| n-Butane (nC4) | 1.86 |
| Trans But-2-ene (t2C4=) | 1.67 |
| But-1-ene (1C4=) | 1.51 |
| isobutylene (iC4=) | 2.61 |
| Cis But-2-ene (c2C4=) | 1.29 |
| 1,3-butadiene | 0.14 |
| Butene (C4=) Liq. | 0.20 |
| Total Gas | 41.01 |
| Gasoline | 45.30 |
| Light cycle oil (LCO) | 10.71 |
| Heavy cycle oil (HCO) | 1.66 |
| Coke | 1.33 |

A Zr-ZSM-5 catalytic composition was prepared with a $SiO_2/Al_2O_3$ molar ratio of 85, and a $SiO_2/ZrO_2$ molar ratio of 42. The Zr-ZSM-5 catalyst was mixed with kaolin in a weight ratio of 1:1 and subject to steaming with saturated steam at 750° C. for 3 hours. The catalyst was tested in a fixed-bed micro-activity flow reactor at 650° C. and a feed injection time of 30 seconds using KGC feed and a catalyst/oil ratio of 8.45. The conversion of KGC feeds was approximately 86.08%. Cracking yields from KGC over Zr-ZSM-5 zeolites are presented in Table 5. This example shows an enhancement of 20 wt % in propylene yields and 39 wt % in ethylene yields by the isomorphously zirconium substituted-ZSM-5.

TABLE 5

| Yield | wt % |
|---|---|
| $H_2$ | 0.38 |
| C1 | 3.85 |
| C2 | 3.69 |
| C2= | 11.27 |
| C3 | 4.06 |
| C3= | 17.77 |
| iC4 | 0.80 |
| nC4 | 2.05 |
| t2C4= | 1.87 |
| 1C4= | 1.70 |
| iC4= | 2.91 |
| c2C4= | 1.43 |
| 1,3-butadiene | 0.18 |
| C4= (Liq.) | 0.12 |
| Total Gas | 52.07 |
| Gasoline | 33.14 |
| LCO | 11.55 |
| HCO | 2.37 |
| Coke | 0.87 |

As shown in Tables 4 and 5, there was approximately 35% reduction in coke formation when the Zr-ZSM-5 catalytic composition was used. The reduction in coke formation is an important advantage of the Zr-ZSM-5 composition over the ZSM-5 composition, as coke formation on the crystal surface of the zeolites obstructs the accessibility of the pores and thus deactivates the catalyst.

Example 2

An experiment was conducted to evaluate the changes in conversion and yield pattern with increasing catalyst/oil ratio from 4.9 to 8.5, using the Zr-ZSM-5 catalytic composition. The yields of the various individual components are presented in Table 6 that shows the yields of the base case catalyst (ZSM-5 zeolites without zirconium) and Zr-ZSM-5 zeolites on the cracking results of KGC. Also shown is the effect of catalyst/oil ratio on the yields using Zr-ZSM-5 catalytic compositions.

TABLE 6

| Description | ZSM-5 | Zr-ZSM-5 | | | |
|---|---|---|---|---|---|
| C/O, ratio | 8.1 | 4.9 | 7.3 | 7.8 | 8.5 |
| Conversion, % | 87.6 | 81.1 | 83.1 | 82.6 | 86.1 |
| Yields | wt % | wt % | wt % | wt % | wt % |
| C3= | 14.9 | 12.7 | 14.1 | 15.6 | 17.8 |
| C2= | 8.2 | 6.3 | 7.3 | 8.9 | 11.3 |
| LPG | 27.4 | 24.4 | 26.8 | 30.0 | 32.9 |
| Dry gas | 13.9 | 11.1 | 12.8 | 15.5 | 19.2 |
| Gasoline | 45.5 | 45.1 | 42.7 | 36.1 | 33.1 |
| LCO | 10.8 | 15.5 | 13.9 | 13.6 | 11.6 |
| HCO | 1.7 | 3.4 | 3.0 | 3.9 | 2.4 |
| Coke | 1.3 | 0.54 | 0.71 | 0.93 | 0.87 |

Conversion % showed an increasing trend with increase in the catalyst/oil ratio of the Zr-ZSM-5 catalytic compositions. Propylene (C3=) and ethylene (C2=) yields showed an increasing trend with increase in the catalyst/oil ratio of the Zr-ZSM-5 catalytic compositions. Similar to the previous results, there was an enhancement of approximately 19 wt % in propylene yields and 38 wt % in ethylene yields when Zr-ZSM-5 composition was used at a catalyst/oil ratio of 8.5 as compared to the unmodified ZSM-5 composition at a catalyst/oil ratio of 8.1. This increase in olefin yields with increase in the catalyst/oil ratio of the Zr-ZSM-5 catalytic compositions corresponded with decreasing gasoline yields.

Ranges may be expressed here as from one particular value and to another particular value. When such a range is expressed, it is to be understood that another embodiment is from the one particular value and to the other particular value, along with all combinations within said range. Where the range of values is described or referenced here, the interval encompasses each intervening value between the upper limit and the lower limit as well as the upper limit and the lower limit and includes smaller ranges of the interval subject to any specific exclusion provided.

The descriptions of methods and apparatuses, and results obtained using them are provided merely as illustrative examples. Descriptions of the methods are not intended to require or imply that the steps of the various embodiments must be performed in the order presented. As will be appreciated by one of ordinary skill in the art, the steps in any particular embodiments may be performed in any order. Words such as "then" are not intended to limit the order of the steps; these words are simply used to guide the reader through the description of the methods. Many of the operations may be performed in parallel or concurrently. In addition, the order of the operations may be re-arranged. While various embodiments have been described in detail for the purpose of illustration, they are not to be construed as limiting, but are intended to cover all the changes and modifications within the spirit and scope of this disclosure.

What is claimed is:

1. A method of catalytic cracking of a hydrocarbon-containing feedstock to catalytic cracking conversion products, the method comprising:

providing, to a catalytic cracking process, a hierarchical zeolite composition prepared by:
  subjecting an initial zeolite and a zirconium source to a partial isomorphous substitution process to produce a zirconium-substituted zeolite;
  subjecting the zirconium-substituted zeolite to a framework modification process using a single template to produce a framework-modified zeolite; and
  subjecting the framework-modified zeolite to an ion exchange process to produce a hierarchical pore structure in at least a portion of the framework-modified zeolite, resulting in the hierarchical zeolite composition; and
contacting a hydrocarbon-containing feedstock with the hierarchical zeolite composition at catalytic cracking conditions to produce catalytic cracking conversion products.

2. The method of claim 1, wherein the initial zeolite is one or more of ZSM-5, ZSM-11, ZSM-12, ZSM-23, ZSM-35, ZSM-38 and ZSM-48.

3. The method of claim 1, wherein the zirconium source is one or more of zirconium chloride, zirconium sulfate, zirconium nitrate, and zirconium oxide.

4. The method of claim 1, wherein the zirconium source is zirconium chloride and the initial zeolite is ZSM-5.

5. The method of claim 1, wherein the single template is a tetra-ammonium salt or hydroxide.

6. The method of claim 1, wherein the framework modification process comprises:
  contacting the zirconium-substituted zeolite with tetrapropylammonium hydroxide (TPAOH) to produce a TPAOH-treated zeolite;
  subjecting the TPAOH-treated zeolite to hydrothermal aging; and
  calcining at least a portion of TPAOH-treated zeolite to produce the framework-modified zeolite.

7. The method of claim 1, wherein the ion exchange process comprises:
  contacting the framework-modified zeolite with an acid to produce a hierarchical pore structure in at least a portion of the framework-modified zeolite, resulting in the hierarchical zeolite composition.

8. The method of claim 1, wherein the ion exchange process comprises:
  contacting the framework-modified zeolite with ammonium chloride to produce a hierarchical pore structure in at least a portion of the framework-modified zeolite, resulting in the hierarchical zeolite composition.

9. The method of claim 1, wherein preparing the hierarchical zeolite composition further includes:
  calcining at least a portion of hierarchical zeolite composition and contacting the hierarchical zeolite composition with steam, before contacting the hierarchical zeolite composition with the hydrocarbon-containing feedstock.

10. The method of claim 1, wherein preparing the hierarchical zeolite composition further includes:
  impregnating at least a portion of hierarchical zeolite composition with one or more of phosphorous, lanthanum, and manganese.

11. The method of claim 1, wherein said catalytic cracking conversion products include olefins having 2 to 4 carbon atoms and yield of said olefins is increased by at least ten percent as compared to yield of said olefins from a catalytic cracking process using the initial zeolite.

12. The method of claim 1, wherein said catalytic cracking conversion products include olefins having 2 to 4 carbon atoms and yield of said olefins is increased by at least twenty percent as compared to yield of said olefins from a catalytic cracking process using the initial zeolite.

13. The method of claim 1, wherein said catalytic cracking conversion products include gasoline and yield of the gasoline is decreased by at least ten percent as compared to yield from a catalytic cracking process using the initial zeolite.

14. The method of claim 1, wherein said catalytic cracking conversion products include gasoline and yield of the gasoline is decreased by at least twenty percent as compared to yield from a catalytic cracking process using the initial zeolite.

15. A method of catalytic cracking of a hydrocarbon-containing feedstock to catalytic cracking conversion products, the method comprising:
  providing, to a catalytic cracking process, a hierarchical zeolite composition prepared by:
    mixing an alumina source, a silica source, and a zirconium source under reaction conditions to produce a zirconium-containing zeolite;
    subjecting the zirconium-substituted zeolite to a framework modification process using a single template to produce a framework-modified zeolite; and
    subjecting the framework-modified zeolite to an ion exchange process to produce a hierarchical pore structure in at least a portion of the framework-modified zeolite, resulting in the hierarchical zeolite composition; and
  contacting a hydrocarbon-containing feedstock with the hierarchical zeolite composition at catalytic cracking conditions to produce catalytic cracking conversion products.

16. The method of claim 15, further comprising:
  steaming the hierarchical zeolite composition and mixing the hierarchical zeolite with kaolin in a 1:1 ratio to form a slurry containing the hierarchical zeolite and kaolin;
  mixing the slurry containing the hierarchical zeolite and kaolin under heat to evaporate water and produce a hierarchical zeolite-kaolin powder mixture; and
  subjecting the hierarchical zeolite-kaolin powder mixture to calcination, before contacting the hierarchical zeolite composition with the hydrocarbon-containing feedstock.

17. The method of claim 15, wherein the zirconium source is one or more of zirconium chloride, zirconium sulfate, zirconium nitrate, and zirconium oxide.

18. The method of claim 15, wherein the alumina source is sodium aluminate.

19. The method of claim 15, wherein the silica source is colloidal silica.

20. The method of claim 15, wherein a first mole ratio of the silica source and the alumina source ranges from 100 to 250 and a second mole ratio of the silica source and the zirconium source ranges from 20 to 250.

* * * * *